(12) United States Patent
Larsen

(10) Patent No.: US 11,306,038 B2
(45) Date of Patent: Apr. 19, 2022

(54) PREPARATION OF $^{212}$PB LABELED MONOCLONAL ANTIBODIES

(71) Applicant: Sciencons AS, Oslo (NO)

(72) Inventor: Roy Hartvig Larsen, Oslo (NO)

(73) Assignee: SCIENCONS AS, Oslo (NO)

( * ) Notice: Subject to any disclaimer, the term of this patent is extended or adjusted under 35 U.S.C. 154(b) by 103 days.

(21) Appl. No.: 16/307,811

(22) PCT Filed: Jun. 23, 2017

(86) PCT No.: PCT/EP2017/065508
§ 371 (c)(1),
(2) Date: Dec. 6, 2018

(87) PCT Pub. No.: WO2017/220767
PCT Pub. Date: Dec. 28, 2017

(65) Prior Publication Data
US 2019/0194087 A1 Jun. 27, 2019

(30) Foreign Application Priority Data
Jun. 24, 2016 (EP) .................................... 16176263

(51) Int. Cl.
*A61K 51/00* (2006.01)
*A61M 36/14* (2006.01)
*C07B 59/00* (2006.01)
*A61K 51/10* (2006.01)

(52) U.S. Cl.
CPC ........ *C07B 59/008* (2013.01); *A61K 51/1051* (2013.01); *A61K 51/1096* (2013.01); *C07B 2200/05* (2013.01)

(58) Field of Classification Search
None
See application file for complete search history.

(56) References Cited

U.S. PATENT DOCUMENTS 9,433,690 B1 * 9/2016 Larsen ............... A61K 51/1051

FOREIGN PATENT DOCUMENTS

| EP | 3061464 A1 | 8/2016 |
| WO | WO 2012/032043 A1 | 3/2012 |

OTHER PUBLICATIONS

Milenic, Diane E. et al., "∝-Particle Radioimmunotherapy of Disseminated Peritoneal Disease Using a $^{212}$Pb-Labeled Radioimmunoconjugate Targeting HER2" Cancer Biotherapy & Radiopharmaceuticals, 2005, pp. 557-568, vol. 20, No. 5.
Ruble, Gaye et al., "The Use of $^{212}$Pb-Labeled Monoclonal Antibody in the Treatment of Murine Erythroleukemia" Int. J. Radiation Oncology Biol. Phys., 1996, pp. 609-616, vol. 34, No. 3.
Westrøm, Sara et al., "Preparation of $^{212}$Pb-labeled monoclonal antibody using a novel $^{224}$Ra-based generator solution" Nuclear Medicine and Biology, 2017, pp. 1-9, vol. 51.
Young, Kwon et al., "Application of $^{212}$Pb for Targeted ∝-particle Therapy (TAT): Pre-clinical and Mechanistic Understanding through to Clinical Translation" AIMS Medical Science, Aug. 2015, pp. 228-245, vol. 2, Issue 3.
International Search Report for PCT/ EP2017/065508 dated Aug. 23, 2017.

\* cited by examiner

*Primary Examiner* — Frederick F Krass
*Assistant Examiner* — Melissa J Perreira
(74) *Attorney, Agent, or Firm* — Knobbe, Martens, Olson & Bear LLP

(57) ABSTRACT

The present invention relates to the generation of lead-212 for therapeutic use. Specifically, are methods related to the generation of lead-212 based radio labelled proteins, such as radioimmunoconjugates, embodiments of the present invention.

15 Claims, No Drawings

PREPARATION OF $^{212}$PB LABELED MONOCLONAL ANTIBODIES

CROSS REFERENCE TO RELATED APPLICATIONS

This application is a U.S. National Phase Application of PCT International Application Number PCT/EP2017/065508, filed on Jun. 23, 2017, designating the United States of America and published in the English language, which is an International Application of and claims the benefit of priority to European Patent Application No. 16176263.8, filed on Jun. 24, 2016. The disclosures of the above-referenced applications are hereby expressly incorporated by reference in their entireties.

FIELD OF THE INVENTION

The present invention relates to the generation of lead-212 for therapeutic use. Specifically, are methods related to the generation of lead-212 based radio labelled proteins, such as radioimmunoconjugates, embodiments of the present invention.

BACKGROUND OF THE INVENTION

Lead-212 ($^{212}$Pb) is a promising therapeutic radionuclide as it decays via short lived alpha emitting daughters resulting in an average of one alpha particle per $^{212}$Pb decay.

The half-life of $^{212}$Pb of 10.6 hours is a limitation to its use and there is a need for fast and safe production and purification procedures. Lead-212 based radioimmunoconjugate is currently in clinical testing against peritoneal cancer using $^{212}$Pb separated from $^{224}$Ra in a cation exchange column and eluted in mineral acid which has to be reconstituted before radiolabeling.

The current method leads to loss due to less than quantitative elution output and time between elution and labelling.

Thus, there is need for new methods that take these issues into account.

SUMMARY OF THE INVENTION

The present invention relates to a method for generating a radionuclide labeled protein, the method comprising; a) providing an aqueous solution comprising 224Ra and $^{212}$Pb, and an aqueous solution or easily dissolvable formulation comprising a proteinconjugated with a chelator, b) mixing and incubation of the solutions provided in a) to provide a reaction solution comprising a radionuclide labeled protein, c) purification of the reaction solution by gel filtration chromatography, and d) recover the radionuclide labeled protein from the purification in step c).

The protein may be selected from the group consisting of a monoclonal antibody, a polyclonal antibody, antibody fragment, a synthetic protein, and a peptide.

The recovered radionuclide labelled protein in step d) may comprise $^{212}$Bi as well as $^{212}$Pb.

In one embodiment of the present invention the solution comprising $^{224}$Ra and $^{212}$Pb in step a) has a radioactivity generated from $^{224}$Ra and $^{212}$Pb of 1 to 10 000 MBq, such as 50 to 1000 MBq per, 1 kBq to 1 GBq, such as 10 kBq to 100 MBq, such as 100 kBq to 10 MBq, such as 10 MBq to 200 MBq.

In another embodiment of the present invention the activity ratio in MBq between $^{212}$Pb to $^{224}$Ra in the aqueous solution in step a) is between 0.5 and 2, such as 0.8-1.5, or such as 0.8-1.3, or preferably such as 0.9-1.15.

In yet another embodiment of the present invention the protein conjugated with a chelator recovered in step d) is present in amount of 0.01-50 mg, such as 0.1-25 mg, such as 0.5-10 mg, such as 1-5 mg.

In a further embodiment of the present invention the solution in step a) is in a volume of 10 µL to 1000 mL, such as 500 µL to 100 mL, such as 1 mL to 10 mL.

In another embodiment of the present invention the solution comprising a protein conjugated with a chelator in step a) has a concentration of 0.1 to 4 mg/ml, such as 0.25 to 2 mg/ml, such as 0.5 to 1.5 mg/ml, such as 0.1 to 10 mg/ml antibody conjugated with a chelator.

In yet another embodiment of the present invention the mixing and incubation in step b) is done in 1-180 minutes, such as 5-120 minutes, such as 15-60 minutes, such as 20-40 minutes, such as 30-60 minutes.

In another embodiment of the present invention the gel filtration chromatography in step c) is selected from the group consisting of desalting purification, desalting and buffer exchange, and desalting gel exclusion separation.

In another embodiment of the present invention the desalting is repeated for enhancement of the purity.

In another embodiment the raw solution to be purified is added a chelator to complex uncomplexed radionuclides to further increase the purity of the final radioconjugate recovered from the desalting step.

In a further embodiment of the present invention the purification in step c) driven by one of the methods selected from the group consisting of centrifugation driven, pressure driven, vacuum driven or gravitation driven.

In another embodiment of the present invention the chelator is TCMC.

In another embodiment of the present invention the antibody is selected from one or more of the group consisting of trastuzumab, rituximab, HH1, cetuximab, bevacizumab, daratumumab, alemtuzumab, Pembrolizumab, Epratuzumab, L19, F8, F16, Galiximab, Toralizumab, Alemtuzumab, Ofatumumab, Veltuzumab, Afutuzumab, Tositumomab, Reditux and Ibritumomab.

In another embodiment of the present invention the antibody is specific for an antigen selected from the group consisting of CD19, CD20, CD22, CD33, CD37, CD38, CD45, CD74, CD138, PSMA, HER-2, EGFR, MUC-1, MUC-18, CEA, FBP, NG2, EPCAM, Syndecan-1, Ca-125, LK-26, HMFG, CS-1, and BCMA.

Another aspect of the present invention relates to a radionuclide labeled protein recovered from a method according to the present invention.

Another aspect of the present invention relates to a kit for the generation of a radionuclide labeled protein comprising an aqueous solution comprising $^{224}$Ra and $^{212}$Pb an aqueous solution comprising an protein conjugated with a chelator, means for gel filtration chromatography, and optionally instructions for the generation of a radionuclide labeled protein.

DETAILED DESCRIPTION OF THE INVENTION

The current methods for the generation of $^{224}$Ra labelled protein, such as an antibody, leads to loss due to less than quantitative elution output and time between elution and labeling.

The object of the present invention is an alternative new and inventive method that take into account these issues.

One solution is a method of in situ labeling of monoclonal protein, such as an antibody, with $^{212}$Pb in $^{224}$Ra solution and subsequently removal of $^{224}$Ra as an alternative strategy for preparing $^{212}$Pb based radiolabelled protein, such as a radioimmunoconjugate.

In the present context is radioimmunoconjugate defined as a substance that comprises a radionuclide, a conjugator, and a protein, such as an antibody. This is also referred to as radionuclide labeled protein, or radionuclide labelled antibody.

The present invention relates to a method for generating a radionuclide labeled protein, the method comprising; a) providing an aqueous solution comprising $^{224}$Ra and $^{212}$Pb, and an aqueous solution or easily dissolvable formulation comprising a protein conjugated with a chelator, b) mixing and incubation of the solutions provided in a) to provide a reaction solution comprising a radionuclide labeled protein, c) purification of the reaction solution by gel filtration chromatography, and d) recover the radionuclide labeled protein from the purification in step c).

The protein may selected from the group consisting of a monoclonal antibody, a polyclonal antibody, antibody fragment, a synthetic protein, and a peptide.

The protein may also be a Glu-urea motif. The Glu-urea motif targets PSMA. The Glu-urea motif targeting PSMA may be selected from the group consisting of PSMA-617, PSMA-11, MIP-1427. The protein may also be selected from the group consisting of biotin or avidin or similar, and folate and derivatives.

The size of the protein of the present invention may be any that is larger than $^{224}$Ra due to the size exclusion discrimination of the present invention. Thus, the size of the protein is larger than about 300 in molecular mass, $M_r$. In one embodiment of the present invention is the size of the protein 500-500.000 in molecular mass, $M_r$. The size may also be 40.000-200.000 or 500-5000 in molecular mass, $M_r$.

In a preferred embodiment of the present invention is the protein an antibody.

In one embodiment of the present invention, the $^{224}$Ra used in the methods of the present invention can be produced using ion exchange chromatography, chelator resin bound $^{228}$Th, e.g., Ac-resin or TRU-resin, or from ThO slurry. ThO slurry is for example described in U.S. Pat. No. 7,887,782.

The present examples show that a TCMC-conjugated protein, exemplified by a monoclonal antibody, can be efficiently labeled with $^{212}$Pb in solutions of $^{224}$Ra in equilibrium with $^{212}$Pb.

Subsequently, the $^{212}$Pb labeled conjugate can be separated from cationic $^{224}$Ra using for example desalting gel exclusion separation. This means that a ready to use $^{224}$Ra/$^{212}$Pb solution can be shipped from a centralized supplier to the end user.

The advantages of using $^{224}$Ra in solution is twofold (1) it is less time consuming to perform the procedures as the acid extraction step is avoided, and (2) it is less laborious and does not require evaporation of acids etc. The yield is also higher.

It is known from studies of using $^{224}$Ra in the treatment of ankylosing spondylitis that modest amounts (typically less than 10 MBq) can be administered to patients without considerable bone marrow toxicity indicating a 1-2% content in a $^{212}$Pb based product, e.g., of 100 MBq, would be acceptable as long as the $^{212}$Pb product do not produce a high degree of bone marrow toxicity.

If a purer product in terms of $^{224}$Ra would needed, repeated purification on a second PD-10 column could accomplish this. Compared with the current ion exchange based generators which may be "milked" several times (although with a rapidly decreasing capacity), the described $^{224}$Ra solution based generator will be for single use only.

Also add a second, preferably a low molecular weight, chelator, e.g., EDTMP to complex uncomplexed radionuclides in the raw solution at the end of the reaction with the conjugate and prior to performing the desalting step can further enhance the final product purity.

Thus, the present examples demonstrate an alternative way of using $^{224}$Ra as a shippable generator for producing $^{212}$Pb-based radioconjugated protein which is simpler and less time consuming compared with current ion exchange based methods.

Concentrations Ratios and Amounts

The radioactivity in the solutions of the methods of the present invention can be of different intensity depending on the intended use. In one embodiment of the present invention the solution comprising $^{224}$Ra and $^{212}$Pb in step a) has a radioactivity generated from $^{224}$Ra and $^{212}$Pb of 1 to 10000 MBq, such as 50 to 1000 MBq per, 1 kBq to 1 GBq, such as 10 kBq to 100 MBq, such as 100 kBq to 10 MBq, such as 10 MBq to 200 MBq.

The radioactivity is in one embodiment 10 kBq to 10 MBq.

The radioactivity is in a preferred embodiment 10 kBq to 100 MBq.

The solutions of the present invention comprising $^{224}$Ra and $^{212}$Pb may be generated from $^{228}$Th.

The recovered radionuclide labelled protein may comprise $^{212}$Bi due to further decay from $^{212}$Pb. Thus, the $^{212}$Bi/$^{212}$Pb ratio of the protein of the composition of the present invention may be $^{212}$Bi/$^{224}$Ra at a ratio of 1/1 within +/−30%. The radio may also be 1/1 within +/−20% or 1/1 within +/−10%.

In one embodiment of the present invention is the recovered radionuclide labeled protein, such as an antibody, scaled in order to the amounts needed for administration and dosing.

Thus, in one embodiment of the present invention is the recovered radionuclide labeled protein, such as an antibody, subsequently formulated as a pharmaceutical composition.

A pharmaceutical composition comprises recovered radionuclide labeled protein, such as an antibody, according to the invention and a diluent, carrier, surfactant, and/or excipient.

Acceptable pharmaceutical carriers include but are not limited to non-toxic buffers, fillers, isotonic solutions, solvents and co-solvents, anti-microbial preservatives, anti oxidants, wetting agents, antifoaming agents and thickening agents etc. More specifically, the pharmaceutical carrier can be but are not limited to normal saline (0.9%), half-normal saline, Ringer's lactate, dissolved sucrose, dextrose, e.g. 3.3% Dextrose/0.3% Saline. The physiologically acceptable carrier can contain a radiolytic stabilizer, e.g. ascorbic acid, human serum albumin, which protect the integrity of the radiopharmaceutical during storage and shipment.

In one embodiment is formulation as a pharmaceutical composition done after the recover step d).

Since the decay series of $^{224}$Ra includes a radon daughter, which may diffuse into the air, vials containing the products must be well sealed to prevent escape of $^{220}$Rn.

Because of the highly localized nature of alpha-irradiation, radiolysis must be considered as a potential problem and the radiopharmaceutical must be designed to minimize this. According to the knowledge in the field, radiolabeled protein, such as antibodies, are sensitive to radiolysis and therefore a kit system may be advantageous for $^{224}$Ra solutions, which are to be combined with chelator conjugated antibodies for scavenging $^{212}$Pb and or $^{212}$Bi.

For a monoclonal antibody it is usually advisable be keep the self-dose of the alpha particle producing radiopharmaceutical solution below 0.5 kGy to avoid reduced binding properties due to radiolysis. Thus, a kit system whereby chelator conjugated protein, such as antibody, is added to the $^{224}$Ra (including daughters) solution a few hours to 10 minutes before injection is advised for concentrated solutions intended for remote shipping.

The pharmaceutical composition prepared with an amount of radionuclide that is 1 kBq to 10 GBq per dosing.

In another embodiment of the present invention the activity ratio in MBq between $^{212}$Pb to $^{224}$Ra in the aqueous solution in step a) is between 0.5 and 2, such as 0.8-1.5, or such as 0.8-1.3, or preferably such as 0.9-1.15. The activity ratio is preferably 0.5 and 2.

The term "activity ratio" e.g. between $^{212}$Pb and $^{224}$Ra relates to the ratio of MBq of $^{212}$Pb to $^{224}$ Ra.

In yet another embodiment of the present invention the protein, such as antibody, conjugated with a chelator recovered in step d) is present in amount of 0.05-50 mg, such as 0.1-25 mg, such as 0.5-10 mg, such as 1-5 mg. The amount is preferably 0.05-50 mg.

In a further embodiment of the present invention the solution in step a) is in a volume of 100 µL to 1000 mL, such as 500 µL to 100 mL, such as 1 mL to 10 mL. The volume is preferably 100 µL to 1000 mL.

In another embodiment of the present invention the solution comprising a protein, such as an antibody, conjugated with a chelator in step a) has a concentration of 0.1 to 4 mg/ml, such as 0.25 to 2 mg/ml, such as 0.5 to 1.5 mg/ml, such as 0.1 to 10 mg/ml protein, such as antibody, conjugated with a chelator. The concentration is preferably 0.1 to 4 mg/ml.

Mixing and Incubation

In yet another embodiment of the present invention the mixing and incubation in step b) is done in 1-180 minutes, such as 5-120 minutes, such as 15-60 minutes, such as 20-40 minutes, such as 30-60 minutes. The time is preferable 30-60 minutes.

The mixing may be done by on an automated shaker. The temperature is preferably 30-40° C., and more preferably 37° C.

Gel Filtration Chromatography

Size-exclusion chromatography (SEC), also known as molecular sieve chromatography, is a chromatographic method in which molecules in solution are separated by their size, and in some cases molecular weight. It is usually applied to large molecules or macromolecular complexes such as proteins and industrial polymers. Typically, when an aqueous solution is used to transport the sample through the column, the technique is known as gel-filtration chromatography, versus the name gel permeation chromatography, which is used when an organic solvent is used as a mobile phase. SEC is a widely used polymer characterization method because of its ability to provide good molar mass distribution (Mw) results for polymers.

Thus, in another embodiment of the present invention the gel filtration chromatography in step c) is selected from the group consisting of desalting purification, desalting and buffer exchange, and desalting gel exclusion separation.

The gel filtration chromatography of the present invention is therefore also known as size-exclusion chromatography (SEC) with use of an aqueous solution for transport through the column.

In another embodiment of the present invention the desalting is repeated for enhancement of the purity. The desalting can be repeated once, twice, three or more times.

In another embodiment a second, preferably a low molecular weight, chelator, e.g., EDTMP is added to complex uncomplexed radionuclides in the raw solution at the end of the reaction with the conjugate and prior to performing the desalting step to further enhance the final product purity.

Examples of columns include the PD10 Desalting column (Sephadex G-25 PD-10 column) and the Econo-Pac 10DG Desalting column (BioRad).

The size ranges for the purification in the method presented herein can vary. In one embodiment is the range 1000-500000 in molecular mass, $M_r$.

The range picked ensures that the radio labelled proteins, such as radioimmunoconjugates, of the present invention are purified. Other ranges may be chosen for optimal purification, for example, 500-5000 in molecular mass, $M_r$, 1000-10000 in molecular mass, $M_r$.

In a further embodiment of the present invention the purification in step c) driven by one of the methods selected from the group consisting of centrifugation driven, pressure driven, vacuum driven or gravitation driven.

Chelator

The radionuclides in the present invention will preferably be conjugated to a protein, such as an antibody, by using chelator, or more preferably bifunctional chelators.

These could be cyclic, linear or branched chelators. Particular reference may be made to the polyaminopolyacid chelators which comprise a linear, cyclic or branched polyazaalkane backbone with acidic (e.g. carboxyalkyl) groups attached at backbone nitrogens.

The chelator of the present invention is suitable for binding $^{212}$Pb. It may be conjugated to the protein by any conventional bonds known to the skilled person, including covalent and electrostatic.

Examples of suitable chelators include DOTA, and DOTA derivatives such as p-isothiocyanatobenzyl-1,4,7,10-tetraazacyclododecane-1,4,7,10-tetraacetic acid (p-SCN-Bz-DOTA) and DTPA derivatives such as p-isothiocyanatobenzyl-diethylenetriaminepentaacetic acid (p-SCN-Bz-DTPA), the first being cyclic chelators, the latter linear chelators.

In one embodiment is the chelator EDTMP or DOTMP.

In another embodiment of the present invention the chelator is (2-(4-isothiocyanatobenzyl-1,4,7,10-tetraaza-1,4,7,10, tetra-(2-carbamonylmethyl)-cyclododecane) also known as TCMC.

Antibody

The antibodies of the present invention may be monoclonal or polyclonal.

In one embodiment of the present invention the antibody is selected from one or more of the group consisting of trastuzumab, rituximab, HH1, cetuximab, bevacizumab, daratumumab, alemtuzumab, Pembrolizumab, Epratuzumab, L19, F8, F16, Galiximab, Toralizumab, Alemtuzumab, Ofatumumab, Veltuzumab, Afutuzumab, Tositumomab, Reditux and Ibritumomab.

In another embodiment of the present invention the antibody is specific for an antigen selected from the group consisting of CD19, CD20, CD22, CD33, CD37, CD38, CD45, CD74, CD138, PSMA, HER-2, EGFR, MUC-1, MUC-18, CEA, FBP, NG2, EPCAM, Syndecan-1, Ca-125, LK-26, HMFG, CS-1, and BCMA.

Radionucleotide Labeled Protein

Another aspect of the present invention relates to a radionuclide labeled protein, such as a radionuclide labeled antibody, recovered from a method according to the present invention.

Another aspect of the present invention relates to a radionuclide labeled protein, such as a radionuclide labelled antibody composition comprising free $^{224}$Ra, and $^{212}$Pb conjugated to an antibody.

In one embodiment of the present invention, this composition comprises less than 10% free $^{224}$Ra.

In one embodiment of the present invention, this composition comprises less than 5% free $^{224}$Ra.

In another embodiment of the present invention, this composition comprises less than 4% free $^{224}$Ra.

In a further embodiment of the present invention, this composition comprises less than 3% free $^{224}$Ra.

In a further embodiment of the present invention, this composition comprises less than 2% free $^{224}$Ra.

In a further embodiment of the present invention, this composition comprises less than 1% free $^{224}$Ra.

In another embodiment of the present invention, this composition comprises more than 0.1% free $^{224}$Ra.

The composition may also comprise 0.1-3% free $^{224}$Ra. This range can also be 0.1-2% free $^{224}$Ra or 0.1-1% free $^{224}$Ra.

The composition may comprise less than 50% free $^{212}$Bi. This amount can also be 10-50% or 30-50%.

Part of the $^{212}$Pb may also be free and not conjugated to the chelator-antibody. The amount of free $^{212}$Pb may therefore be less than 20%, such as less than 10%.

Thus an aspect of the present invention relates to a radionuclide labelled protein composition comprising: $^{212}$Pb conjugated to a protein, $^{212}$Bi conjugated to a protein, 0.1%-2% free $^{224}$Ra, less than 50% free $^{212}$Bi, and less than 20% free $^{212}$Pb.

The term "free" refers to radionuclide that is not bound to chelator-antibody. It can be measured by the techniques described herein and known a person skilled in the art.

Kits

Another aspect of the present invention relates to a kit for the generation of a radionuclide labeled protein, such as, a radionuclide labeled antibody comprising an aqueous solution comprising $^{224}$Ra and $^{212}$Pb, an aqueous solution comprising a protein, such as an antibody, conjugated with a chelator, means for gel filtration chromatography, and optionally instructions for the generation of a radionuclide labeled protein, such as a radionuclide labeled antibody.

In an embodiment, the kit comprises a vial comprising a neutralizing solution to adjust pH and/or isotonicity of the radiopharmaceutical solution prior to administration to a patient.

In one embodiment of the present invention, the chelator conjugated protein, such as an antibody, is added to the $^{224}$Ra and $^{212}$Pb solution 30 min to 60 minutes before recovery of radioconjugated protein, or radioimmunoconjugate.

In one embodiment of the present invention, the chelator conjugated protein, such as an antibody, is added to the $^{224}$Ra and $^{212}$Pb solution 1 min to 45 min before recovery of radioimmunoconjugate.

In one embodiment of the present invention, the chelator conjugated protein, such as an antibody is added to the $^{224}$Ra and $^{212}$Pb solution 20 min to 45 min before recovery of radioimmunoconjugate.

General

It should be understood that any feature and/or aspect discussed above in connections with the compounds according to the invention apply by analogy to the methods described herein.

The terms X and Y, are used interchangeably.

The following figures and examples are provided below to illustrate the present invention. They are intended to be illustrative and are not to be construed as limiting in any way.

EXAMPLES

Example 1—Radioactivity Measurements

γ-spectroscopy was performed with a liquid nitrogen cooled high purity germanium well detector system (GWC6021, Canberra Industries, Meriden Conn., USA) coupled to a DSA 1000 digital signal analyzer. Spectra were analyzed with the Genie 2000 software (version 3.1, Canberra Industries, Meriden Conn., USA).

A radioisotope calibrator (CRC-25R, Capintec Inc., Ramsey, N.J., USA) was used to measure higher amounts of radioactivity.

Radioactive samples were counted on a Cobra II Autogamma counter (Packard Instruments, Downer Grove, Ill., USA) or a Hidex Automatic Gamma Counter (Hidex, Turku, Finland).

Example 2—the $^{224}$Ra-Generator

The $^{224}$Ra generator consisted of a $^{228}$Th source packed together with an actinide resin on a column. The column retains $^{228}$Th whereas $^{224}$Ra (plus daughter(s)) can be eluted 1 M HCl. All work with concentrated radioactive preparations, including evaporation of solvent, was performed in a glove-box.

A source of $^{228}$Th in 1 M HNO$_3$ was acquired from a commercial supplier and an actinide resin based on the DIPEX® Extractant was obtained from Eichrom Technologies LLC (Lisle, Ill., USA) in the form of pre-packed cartridges of 2 ml. The material in an actinide resin cartridge was extracted and the resin was preconditioned with 1 M HCl. To use smaller volume of solvent, approximately 25% (0.5 ml) of the resin was repacked in a smaller 1 ml column, Isolute SPE, Biotage AB, Uppsala, Sweden). The inactive resin was introduced in the bottom of the column to serve as a catcher layer for small amounts of $^{228}$Th in the case of some release of $^{228}$Th during operation of the generator. A slurry of approximately 40% (0.4 ml) of the cartridge content and 600 μl $^{228}$Th in 0.1 M HNO$_3$ was prepared in a vial (4 ml vial, E-C sample, Wheaton, Millville, N.J., USA) and incubated with gentle agitation for the immobilization of $^{228}$Th for at least 4 hours. Afterwards the radioactive slurry was loaded onto the column.

Radium could be eluted regularly from this column with 2 ml of 1 M HCl. For further purification, the 2 ml crude 1 M HCl was used without evaporation and loaded onto a second actinide resin cartridge which was washed with additional 0.5 ml 1 M HCl to produce an eluate of 2.5 ml containing $^{224}$Ra. This solution was evaporated to dryness, using a heater block and flushing the vial with N$_2$ gas through a Teflon tube inlet and outlet in the rubber/Teflon septum on the vial and by leading the acid vapor into a beaker of saturated NaOH by a stream of $_{N2}$-gas. The residue after evaporation was dissolved in 0.2 ml or more of 0.1 M HCl.

Possible breakthrough of $^{228}$Th in eluates was investigated by storing samples from the eluate for minimum 10 half-lives of $^{224}$Ra (36 days) and then the activity was assayed.

Purity of $^{224}$Ra Solutions.

By storing 5% samples of the $^{224}$Ra solution produced the purity of $^{224}$Ra vs. 228Th could be assessed. Five randomly selected samples were used which had been stored for at least three months and any $^{228}$Th present would be in equilibrium with $^{224}$Ra and daughters at the time of measurement. The measurements were performed using the Hidex gamma counter that had been calibrated for $^{228}$Th.

Example 3—Radiolabeling of Antibodies

The humanized anti-HER2 IgG1 monoclonal antibody trastuzumab (Herceptin, Roche, Basel, Switzerland) conjugated to a chelator, TCMC (2-(4-isothiocyanatobenzyl-1,4, 7,10-tetraaza-1,4,7,10,tetra-(2-carbamonylmethyl)-cyclododecane) was used for radiolabeling with $^{212}$Pb. Before conjugation to TCMC, the buffer of a trastuzumab sample was exchanged to carbonate buffer (0.1M NaHCO$_3$ and 5 mM Na$_2$CO$_3$ in metal free water) by washing 4 times with a centrifugal concentrator (Vivaspin 15R, 50 kDa MWCO, Sartorius Stedim Biotech, Göttingen, Germany). After buffer exchange the antibody concentration was determined with spectrophotometry. A solution of TCMC dissolved in 5 mM HCl was added to trastuzumab in carbonate buffer in a 5-fold molar excess of chelator to antibody. The mixture was allowed to react for 2 h during gentle agitation at room temperature. To separate unconjugated chelator from TCMC-trastuzumab and at the same exchanging the carbonate buffer to 0.9% NaCl, a centrifuge filtering cartridge (Vivaspin 15R, 50 kDa MWCO) was used. The sample was diluted 1:10 with 0.9% NaCl and the antibody conjugate was concentrated 10 times by centrifugation. This procedure was repeated a total of three times. The TCMC-trastuzumab conjugate was stored at 4° C. until radiolabeling.

A solution of $^{224}$Ra in equilibrium with daughter nuclides was buffered with 10% 5 M NH$_4$OAc. The pH of the solution was verified to be between 5-6 using pH. TCMC-trastuzumab and the radioactive solution was mixed and incubated for minimum 30 min on a Thermoshaker at 750 rpm and 37° C. In the following this solution consisting of $^{212}$Pb-labeled trastuzumab and free $^{224}$Ra and daughter nuclides is referred to as the "reaction mixture". The labeling was performed with different TCMC-trastuzumab concentrations in the final reaction mixture, ranging from 0.1 to 4 mg/ml.

Example 4—Instant Thin Layer Chromatography Assay Procedure

The radiochemical purity of the $^{212}$Pb labeled antibody in the reaction mixture was evaluated with instant thin layer chromatography (ITLC) strips (model #150-772, Biodex Medical Systems Inc, Shirley, N.Y., USA). An aliquot of reaction mixture was mixed with a 2 fold-excess (by volume) of formulation buffer consisting of 7.5% human serum albumin and 5 mM EDTA in DPBS and adjusted to approximately pH 7 with NaOH. The mixture was whirlmixed for 4-5 sec and left for another 5-10 min. A strip was spotted with typically 1-4 μl of sample at the origin line and placed in a small beaker with about 0.5 ml of 0.9% NaCl for development. After the solvent front had moved to the designated solvent front line, the strip was cut in half at the cut line and each half was placed in a 5 ml test tube for counting. In this system $^{212}$Pb-labeled antibody does not migrate from the bottom half while $^{212}$Pb complexed with EDTA migrates to the upper half.

Example 5—Purification of Radiolabeled Antibodies

The desired end-product of the process described in this study is a pure solution of $^{212}$Pb-labeled TCMC-trastuzumab. To achieve this our reaction mixture needs to be purified to remove free $^{224}$Ra and other unconjugated daughter nuclides. Two different purification methods were evaluated; purification by centrifugal concentration and purification with a desalting column.

Purification by centrifugal concentration was performed with Vivaspin4 with 50 kDa MWCO. The reaction mixture was loaded in the concentrator spin tube and diluted with 0.9% NaCl until the total volume was 4 ml. The content was further concentrated approximately 10 times by centrifugation. Both the filtrate and purified antibody solution was collected and the radioactivity was measured. From these measurements the yield of the process was estimated:

$$\% \ ^{212}Pb\text{-}TCMC\text{-trastuzumab recovered} = \frac{\text{cpm } Ab \text{ after concentrating}}{\text{total cpm applied in spin column}}$$

The samples were then allowed to decay for minimum 48 hours in order to establish equilibrium between $^{224}$Ra and $^{212}$Pb, before they were re-measured and the percentage of 224Ra in the purified antibody solution was calculated:

$$\% \ ^{224}Ra \text{ in recovered } Ab = \frac{\text{cpm } Ab \text{ after concentrating at eq.}}{\text{total cpm applied in spin column at eq.}}$$

A Sephadex G-25 PD-10 column (Amersham Biosciences; Uppsala, Sweden) was used for purification of the reaction mixture. First, the column was equilibrated according to the manufacturer's protocol using Dulbecco's PBS supplemented with 0.5% BSA as the elution buffer. PD10 purification was performed both on the crude reaction mixture and on reaction mixture added a 10 fold-excess (by volume) of formulation buffer.

The formulation buffer contained EDTA for complexing with free radionuclides and the mixture was allowed to react for minimum 10 minutes before application on the PD10 column. The reaction mixture was loaded onto the top of the column and allowed to enter the column completely before additional elution buffer was added. The elution process was continued until 7 fractions of 1 ml each was collected in Eppendorf tubes for further radioactivity measurements. The radiolabeled antibody was typically eluted in fractions 3-5, and the yield of the process was estimated from the measurements:

$$\% \ ^{212}Pb\text{-}TCMC\text{-trastuzumab in fraction 3-5} = \frac{\text{cpm in fraction 3-5}}{\text{total cpm applied to } PD10 \text{ column} \times RCP}$$

RCP of the product in fraction 4 was determined by the previously described ITLC procedure. The samples were then allowed to decay for minimum 48 hours in order to establish equilibrium between $^{224}$Ra and $^{212}$Pb, before they were re-measured and the percentage of $^{224}$Ra in fraction 3-5 was calculated:

$$\% \ ^{224}Ra \ \text{in fraction 3-5} = \frac{\text{cpm in fraction 3-5 at eq.}}{\text{total cpm applied to } PD10 \text{ column at eq.}}$$

Example 6—Results

Radiochemical Purity of $^{224}$Ra

For all five samples measured of retrospectively the $^{228}$Th was below the detection limit estimated to 1 Bq per MBq of $^{224}$Ra (decay corrected). Thus, the purification method seems well suited for preparing $^{224}$Ra for biomedical applications.

Lead-212 Labeling of TCMC-Trastuzumab.

The labeling of $^{212}$Pb in solutions with the presence of $^{224}$Ra worked well with yield above 90% at 0.15 mg per ml, and above, of antibody conjugate (Table 1).

Purification of $^{212}$Pb-labeled antibody conjugate from present $^{224}$Ra cations using microconcentration centrifugation device. The data for concentration and separation of $^{212}$Pb-labeled trastuzumab for cationic $^{224}$Ra is presented in Table 2. As can been seen there is a significant loss of about one third of the $^{212}$Pb-labeled trastuzumab due to the procedure. The separation of $^{224}$Ra from the radioconjugate is 75% completed which indicate that the ratio of $^{212}$Pb-labeled trastuzumab to $^{224}$Ra improves from 1:1 to about 3:1 which is not satisfactory for the biomedical use of $^{212}$Pb-labeled radioimmunoconjugates.

Purification of $^{212}$Pb-labeled antibody conjugate from present $^{224}$Ra cations using desalting with PD-10 gel filtration single use column.

The data for concentration and separation of $^{212}$Pb-labeled trastuzumab for cationic 224Ra is presented in Table 2. The recovery of $^{212}$Pb-trastuzumab is typically 80% or better which is quite favorable. Also the RCP of $^{212}$Pb-trastuzumab tends to increase to above 95%. Moreover, the removal of $^{224}$Ra from the solution is highly effective with typically less than 2% eluting in the $^{212}$Pb-trastuzumab fractions when EDTA was used to quench the reaction mixture. Thus, the use of PD-10 purified $^{212}$Pb-trastuzumab prepared from $^{224}$Ra/$^{212}$Pb mixtures could be feasible.

TABLE 1

Labeling of TCMC-antibody conjugate with $^{212}$Pb in $^{224}$Ra solution

|  |  | RCP % | n |
|---|---|---|---|
| TCMC-trastuzumab | 0.1 mg/ml | 34 ± 23 | 2 |
|  | 0.15 mg/ml | 90 | 1 |
|  | 0.20 mg/ml | 94 | 1 |
|  | 0.25 mg/ml | 93 ± 2.5 | 5 |
|  | 1 mg/ml | 96 ± 0.4 | 4 |
|  | 4 mg/ml | 95 ± 1.2 | 4 |
|  | 5.9 mg/ml | 97 | 1 |
| Trastuzumab | 4 mg/ml | ± |  |
| Negative control, only radioactive solution |  | 3.4 ± 1.2 | 3 |

TABLE 2

Purification of $^{212}$Pb-labeled TCMC-antibody conjugate for $^{224}$Ra solution using centrifugation microconcentrator.

| TCMC-Trastuzumab applied | Mixed with EDTA | Pre-treatment of concentrator | n | % Ab recovered | % 224Ra in recovered Ab | Times concentrated |
|---|---|---|---|---|---|---|
| 7.5 µg | Yes | No | 1 | 72% | 25% | 1 × 10 |
| 20-30 µg | Yes | No | 2 | 66 ± 8% | 22 ± 15% | 1 × 10 |
| 20 µg | Yes | BSA/DPBS | 1 | 60% | 14% | 1 × 10 |
| 80 µg | No | No | 1 | 38% | 4% | 2 × 10 |
| 120 µg | Yes | No | 1 | 81% | 48% | 1 × 10 |

PD10:

TABLE 3

Purification of $^{212}$Pb-labeled TCMC-antibody conjugate for $^{224}$Ra solution using Sephadex G-25 PD 10 gelfiltration desalting single use columns.

| TCMC-Trastuzumab applied | Mixed with EDTA | n | % Ab in fraction 3-5 | % $^{224}$Ra in fraction 3-5 | RCP |
|---|---|---|---|---|---|
| 2 µg | No | 1 | 112% | 0.2% | 94% |
| 2 µg | Yes | 1 | 110% | 1.0% | 99% |
| 5 µg | No | 1 | 86% | 1.6% | 100 ± 0.8% |
| 5 µg | Yes | 1 | 78% | 1.9% | 98 ± 0.9% |
| 80 µg | No | 2 | 75 ± 9.7% | 5.7 ± 7.6% | 95% |
| 80 µg | Yes | 1 | 69% | 0.5% | 97% |

Example 7—Discussion

The current study shows that a TCMC-conjugated monoclonal antibody can be efficiently labeled with $^{212}$Pb in solutions of $^{224}$Ra in equilibrium with $^{212}$Pb. Subsequently, the $^{212}$Pb labeled conjugate can be separated from cationic $^{224}$Ra using desalting gel exclusion separation. This means that a ready to use $^{224}$Ra/$^{212}$Pb solution can be shipped from a centralized supplier to the end user. The advantages of using $^{224}$Ra in solution is twofold (1) it is less time consuming to perform the procedures as the acid extraction step is avoided, and (2) it is less laborious and does not require evaporation of acids etc. It is known from studies of using $^{224}$Ra in the treatment of ankylosing spondylitis that modest amounts (typically less than 10 MBq) can be administered to patients without considerable bone marrow toxicity (3) indicating a 1-2% content in a $^{212}$Pb based product, e.g., of 100 MBq, would be acceptable as long as the $^{212}$Pb product do not produce a high degree of bone marrow toxicity. If a purer product in terms of $^{224}$Ra would needed, repeated purification on a second PD-10 column could accomplish this. Compared with the current ion exchange based generators which may be "milked" several times (although with a rapidly decreasing capacity), the described $^{224}$Ra solution based generator will be for single use only. In conclusion, the current work demonstrates an alternative way of using $^{224}$Ra as a shippable generator for producing $^{212}$Pb-based radioimmunoconjugate which may be simpler and less time consuming compared with current ion exchange based methods.

Example 8—Preparation of $^{212}$Pb-Labeled Monoclonal Antibody Using a Novel $^{224}$Ra-Based Generator Solution Methods Radioactivity Measurements Radioactive samples were measured in the 70-80 keV window on a Cobra II Autogamma counter (Packard Instruments, Downer Grove, Ill., USA) or in the 60-110 keV and 520-640 keV windows on a Hidex Automatic Gamma Counter (Hidex, Turku, Finland). The energy ranges below 110 keV were assumed to mainly count γ radiation from $^{212}$Pb with very small contribution from other radionuclides in the series. Since $^{224}$Ra decay has a modest γ emission in an energy region with more abundant γ from $^{212}$Pb, the $^{224}$Ra activity was determined indirectly from the counts in the 70-80 keV or 60-110 keV window. This was performed by re-measuring the samples after 3 days or more, when the initial $^{212}$Pb present in the sample had decayed and equilibrium between $^{224}$Ra and newly produced $^{212}$Pb had been reached. The 520-640 keV window was evaluated for determining $^{212}$Bi indirectly from the highly abundant $^{208}$Tl γ. Samples of $^{212}$Bi were kept for approximately 20 minutes and then measured to obtain transient equilibrium between $^{212}$Pb and $^{208}$Tl $^{212}$Bi. In Table 1 γ-rays in the $^{224}$Ra-series with higher abundancy than 1% are presented. It shows an overview of radionuclides having X- and/or γ-rays within the 60-110 and 520-640 keV windows. Amounts of radioactivity exceeding 50 kBq were measured by a radioisotope calibrator (CRC-25R, Capintec Inc., Ramsey, N.J., USA).

The $^{224}$Ra-Generator

Thorium-228 (Eckert & Ziegler, Braunschweig, Germany) was immobilized on a DIPEX® (Eichrom Technologies LLC, Lisle, Ill., USA) actinide resin inside a column cartridge. By eluting the cartridge with HCl, 224Ra was extracted from the generator. The details of the $^{224}$Ra-generator setup have been presented elsewhere (U.S. Pat. No. 9,433,690 B1).

Radiolabeling of Antibodies

The monoclonal antibody trastuzumab (Herceptin, Roche, Basel, Switzerland) was conjugated to a chelator, TCMC (Macrocyclics Inc., Dallas, Tex., USA), and used for radiolabeling with $^{212}$Pb.

The original buffer of trastuzumab was exchanged with carbonate buffer (0.1 M NaHCO$_3$ and 5 mM Na$_2$CO$_3$ in metal free water of pH. Eur grade) prior to TCMC labeling. The solution of trastuzumab was washed and concentrated four times with carbonate buffer using a centrifugal concentrator (Vivaspin 15R, 30 or 50 kDa MWCO, Sartorius Stedim Biotech, Göttingen, Germany). During each repeated step trastuzumab was concentrated by a factor of ten. UV-spectrophotometry (Hitachi U-1900, Hitachi High-Technologies Corporation, Tokyo, Japan) using the standard absorbance value of 1.4 for immunoglobulins at 280 nm for 0.1% solutions was used for concentration measurements. To conjugate the TCMC to the antibody, a solution of TCMC dissolved in 5 mM HCl was added to trastuzumab in carbonate buffer in a five- to tenfold molar excess. After the mixture had reacted for 2 h at room temperature with gentle agitation, the unconjugated chelator was separated from TCMC-trastuzumab and the pH reduced by exchanging the carbonate buffer with 0.9% NaCl, using a centrifugal concentrator cartridge (Vivaspin 15R, 30 or 50 kDa MWCO) in repeated fashion as described above. The TCMC-trastuzumab conjugate was stored in a refrigerator until radiolabeling.

Radium-224 in equilibrium with progeny in 0.1 M HCl and 0.5 M NH$_4$OAc was used for radiolabeling. The pH of the solution was verified to be approximately 5-6 using pH paper (Merck Millipore general pH indicator paper, Merck KGaA, Darmstadt, Germany). TCMC-trastuzumab was incubated with $^{224}$Ra-solution for minimum 30 min on a ThermoMixerR (Eppendorf AG, Hamburg, Germany) at 37° C. and 750 rpm. This solution, is referred to as the "reaction mixture". Different concentrations of TCMC-trastuzumab conjugate (in the range from 0.1 to 6 mg/mL) in $^{224}$Ra solution were tested with the described method. Typically, the reaction mixture volume was between 30-130 µLI.

In a special experiment to evaluate $^{212}$Pb and $^{212}$Bi labeling of TCMC-trastuzumab (4 mg/ml), samples were removed from the reaction vial after 5 minutes, 15 minutes and 25 minutes and analyze by instant thin layer chromatography.

In addition a radiolysis experiment was done by letting the reaction mixture incubate overnight to obtain elevated radiation dosing to the radiolabeled product. Subsequently the product was analyzed by High-performance liquid chromatography. In addition the immunoreactive fraction was determined using antigen positive tumor cells by using a one point assay as previously described (https://www.ncbi.nlm.nih.gov/pubmed/27776176).

Instant Thin Layer Chromatography Assay Procedure

The labeling yield also denoted radiochemical purity (RCP) of the $^{212}$Pb labeled antibody in the reaction mixture was measured by instant thin layer chromatography (ITLC) strips (model #150-772, Biodex Medical Systems lnc, Shirley, N.Y., USA). A sample of reaction mixture was mixed with a twofold-excess of formulation buffer (FB) consisting of 7.5% human serum albumin, 5 mM EDTA in Dulbecco's PBS, and adjusted to pH 7 with NaOH. The reaction mixture/FB was shaken for about 5 sec and left for at least 5 min to allow unbound radioisotopes form complex with EDTA. An ITLC strip was spotted with typically 3 µL of sample at the origin line and placed in a small beaker with a small amount of 0.9% NaCl for development. After the solvent front had moved almost to the top, the strip was withdrawn and cut in half at the cut line and each half was placed in a glass tube for counting. In this system $^{212}$Pb-TCMC-trastuzumab stays immobile at the bottom half (B) whereas $^{212}$Pb (and other free radionuclides) complexed with EDTA migrates to the upper half (U). The fraction of $^{212}$Pb as percentage attached to the antibody was determined as:

$$\% \, RCP = \frac{CPM(B)}{CPM(B) + CPM(U)} \times 100$$

where CPM represents count rate per minute.

Determination of Immunoreactive Fraction

The immunoreactive fraction of $^{212}$Pb-TCMC-trastuzumab was determined in a one-point, cell binding assay, performed as previously published (Westrøm et al 2016). In short, samples of 16-20×10$^6$ HER2 expressing human osteosarcoma cells, OHS, incubated at room temperature with $^{212}$Pb-TCMC-trastuzumab or blocked with an excess of trastuzumab prior to adding $^{212}$Pb-TCMC-trastuzumab. The total activity applied before washing and the bound activity after washing was determined for each sample, and the immunoreactive fraction of $^{212}$Pb-TCMC-trastuzumab was estimated to be the fraction determined by total bound after wash divided by the total applied before and minus the same fraction determined for the blocked samples.

High-Performance Liquid Chromatography

The high-performance liquid chromatography (HPLC) system consisted of a 1260 Infinity VL System combined with a size exclusion TSKgel G3000SWxl column (Tosoh Bioscience, product number 08541) an UV (220 and 280 nm) and a radiometric (Radiomatic 150TR Flow Scincillator Analyzer, Perkin Elmer) detector. Mobile phase was made from 50 mM sodium phosphate (pH 7.0) containing 250 mM NaCl A flow rate of 0.8 ml/min was used.

Purification of Radiolabeled Antibodies

The purification was performed using either a centrifugal concentrator and purification or a desalting column. When using centrifugal concentration, the reaction mixture was loaded in a concentrator spin tube (Vivaspin 4, 50 kDa MWCO, Sartorius Stedim Biotech, Gottingen, Germany) and diluted with 0.9% NaCl until the total volume was 4 mL. The content was concentrated tenfold by centrifugation. The concentrate (C) was collected and measured immediately (t=0). The yield (Y) of the purification process was estimated as the percentage of antibody-bound $^{212}$Pb-activity in the concentrate:

$$\% \ Y(^{212}Pb\text{-}TCMC\text{-trastuzumab}) = \frac{CPM(C)_{t=0}}{CPM(T)_{t=0} \times RCP_{reaction \ mixture}} \times 100$$

The total activity (T) loaded onto the centrifugal concentrator was determined from a sample withdrawn from the reaction mixture taken prior to purification which was sealed. A minimum of 3 days after the first measurement (t=eq), when equilibrium between $^{224}$Ra and $^{212}$Pb had been reached, all samples were measured again and the percentage of $^{224}$Ra remaining in the concentrate was calculated:

$$\% \ ^{224}Ra = \frac{CPM(C)_{t=eq}}{CPM(T)_{t=eq}} \times 100$$

In the alternative purification method evaluated a Sephadex G-25 PD-10 column (GE Healthcare Bio-Sciences AB, Uppsala, Sweden) for separation of the radiolabeled TCMC-trastuzumab from unbound radionuclides was used. The column was washed with at least 20 mL of Dulbecco's PBS supplemented with 0.5% bovine serum albumin before being used for purification purposes. The crude reaction mixture as well as reaction mixture added formulation buffer was purified with PD-10. The reaction mixture was reacted with formulation buffer for at least 10 min to allow EDTA to form complexes with unbound radioisotopes before application.

When using PD-10 columns for purification, the sample was loaded on top of the column and allowed to enter the column bed completely before more elution buffer was added. The elution process was continued until at least seven fractions of 1 mL each was collected in Eppendorf tubes. The activity in all fractions were measured immediately. Radiolabeled antibody was usually eluted in fractions 3-5 (F3-F5). This was confirmed with TLC analyses. The yield of the process was estimated to be the percentage of antibody-bound $^{212}$Pb-activity in these fractions vs. total applied $^{212}$Pb activity:

$$\% \ Y(^{212}Pb\text{-}TCMC\text{-trastuzumab}) = \frac{CPM(F3 + F4 + F5)_{t=0}}{CPM(T)_{t=0} \times RCP_{reaction \ mixture}}$$

The total applied $^{212}$Pb activity (T) loaded onto the PD-10 column was determined from a sealed reference sample prepared from an aliquot of the reaction mixture taken prior to purification. RCP of the product in fraction 4 was determined by the previously described ITLC procedure. After at least 3 days, the samples were re-measured and the percentage of $^{224}$Ra remaining in fraction 3-5 was calculated:

$$\% \ ^{224}Ra = \frac{CPM(F3 + F4 + F5)_{t=eq}}{CPM(T)_{t=eq}}$$

To assess co-elution of radionuclides with the protein fractions an experiment was performed where the radiolabeling and PD-10 purification were performed as described above, but unconjugated trastuzumab was used instead of TCMC-conjugated trastuzumab. The presence of $^{212}$Pb and $^{212}$Bi in the seven collected fractions was determined by measurement in the 60-110 and 520-640 keV windows. By measuring the samples 5 min, 20 min, 1 h, 1 day and 5 days after the PD-10 purification was finalized, the decay rate could also be assessed. This was necessary to ascertain if the γ activity in the 520-640 keV window was reflecting the presence of $^{212}$Bi in addition to $^{208}$Tl. From the day 5 measurements, when all samples had reached equilibrium, the amount of $^{224}$Ra was determined.

Retention of the α-Emitting $^{212}$Pb Daughter $^{212}$Bi by the TCMC-Chelator

In a $^{224}$Ra-solution in equilibrium the ratio of $^{212}$Bi activity to $^{212}$Pb activity is approximately equal to one. A sealed $^{224}$Ra sample in equilibrium with progeny was used as a reference to determine an efficiency factor (Bq/cpm) for the 60-110 and 520-640 keV windows. After PD-10 purification of reaction mixture quenched with EDTA, fraction 4 was measured 10 min, 20 min, 60 min and 22 h after end of purification. The $^{212}$Bi to $^{212}$Pb ratio at the different time points was estimated using the efficiency factors. An online universal decay calculator (http://www.wise-uranium.org/rcc.html) was used to determine the theoretical $^{212}$Bi to $^{212}$Pb ratios as a function of time based on different initial $^{212}$Bi to $^{212}$Pb-ratios, ranging from a sample of pure $^{212}$Pb without any $^{212}$Bi present to a sample where the activity ratio is equal to one. Under the assumption that all activity in fraction 4 straight after purification was bound to the antibody-conjugate, an estimate of the portion of $^{212}$Bi retained in the TCMC-chelator could be deduced by comparing the experimentally determined ratios with plots of ingrowth for different theoretical $^{212}$Bi to $^{212}$Pb ratios.

Results and Discussion

Radiolabeling of TCMC-trastuzumab with $^{212}$Pb in a solution of $^{224}$Ra in equilibrium with daughter nuclides was successful. The procedure yielded a product with RCP above 90% already at 0.15 mg/mL of antibody conjugate, and above 95% from 1 mg/mlmL and at higher concentration. In three of the labeling experiments, the immunoreactive fraction of the product was determined. It ranged from 57-66%, which is in line with previously published results on the immunoreactivity of $^{212}$Pb-TCMC-trastuzumab.

Because the labeling was performed in a solution of $^{224}$Ra in equilibrium with daughters, $^{212}$Bi will be present during the incubation. The RCP was therefore also measured in the $^{208}$Tl window after secular equilibrium was reached to account for $^{212}$Bi. This resulted in values ranging from 50-80. At 4 mg per ml TCMC-trastuzumab concentration it was found that $^{212}$Pb was complexed quantitatively already after 5 minutes of reaction and that more than 80% of the $^{212}$Bi was complexed too.

The successful $^{212}$Pb-labeling over a range of antibody concentrations demonstrates that a variety of specific activities of the radioimmunoconjugate can be achieved.

Since this study mainly was intended to show proof of concept, relatively low activity levels were used compared to what is expected in a clinical setting. The radiolabeling was therefore performed in quite small volumes, typically from 30-130 µL, in order to simulate relevant clinical activity concentrations. Due to the low volumes, it was possible to achieve relatively high specific activities of the end product, despite the low activity used. The highest specific activity of $^{212}$Pb-TCMC-trastuzumab achieved in this study was approximately 30 MBq/mg which is comparable to what was used in a recent clinical study with $^{212}$Pb-TCMC-trastuzumab.

Upon complete decay of $^{224}$Ra, stable $^{208}$Pb is formed, which can compete with $^{212}$Pb on conjugation to the TCMC chelator. With the activity levels used here, there was no indication that the presence of $^{208}$Pb influenced the yield of the radiolabeling due to the relatively high specific activity it was possible to achieve. However, the situation might differ when higher $^{224}$Ra activity is used and the following estimation was made: Assume 1 mg antibody labeled in a solution of 100 MBq $^{224}$Ra. This corresponds to $4\times10^{15}$ molecules, where we can assume 2-5 TCMC chelators per antibody, giving $8\text{-}20\times10^{15}$ available binding sites for lead. Complete decay of 100 MBq $^{224}$Ra will form approximately $4.5\times10^{13}$ $^{208}$Pb atoms. These numbers indicate that the presence of 208Pb should not influence the yield of the radiolabeling to a significant extent.

The desired end-product of the process described in this study is a solution of pure $^{212}$Pb-labeled TCMC-antibody. To achieve the desired end-product, the solution with $^{212}$Pb-labeled antibody conjugate was purified to remove free $^{224}$Ra and other unconjugated daughter nuclides. Two different purification methods were evaluated; purification by centrifugal concentration and purification with a desalting column. Both methods are based on a size-dependent separation of the antibody-conjugate from low molecular weight compounds such as free ions, unbound chelator molecules and salts.

Use of the centrifugal concentrator for separation of $^{212}$Pb-TCMC-trastuzumab from cationic $^{224}$Ra and other unconjugated daughter nuclides yielded 70.5±9.6% (n=6) of the antibody-bound $^{212}$Pb activity in the concentrate. The loss of approximately one third of $^{212}$Pb-labeled trastuzumab due to the procedure is significant, but still in line with reported yields (73±3%) of $^{212}$Pb-TCMC-trastuzumab after PD-10 column purification. The amount of $^{224}$Ra remaining in the concentrate was 25.9±13.1% (n=6), i.e. the separation of $^{224}$Ra from the radioimmunoconjugate was only 75% complete. The ratio of $^{212}$Pb-TCMC-trastuzumab to $^{224}$Ra improved from 1:1 to only about 3:1, which is not a satisfactory result for biomedical use of $^{212}$Pb-labeled radioimmunoconjugates. We observed in addition a slight trend towards higher percentage of $^{224}$Ra remaining in the concentrate after purification when higher amounts of antibody-conjugate were applied. This observation might indicate a saturation or clogging of the membrane with protein which decreases the efficiency of filtration of ions through the membrane.

Separation of $^{212}$Pb-TCMC-trastuzumab from $^{224}$Ra and other unconjugated daughter nuclides was more successful when a PD-10 gel filtration column was used. The use of gel filtration columns like PD-10 is common for purification of radiolabeled antibodies and allows rapid removal of low molecular weight substances, such as unconjugated radionuclides, from the antibody containing solutions. The recovery of $^{212}$Pb-trastuzumab was very favorable, with a yield of approximately 80% in fraction 3-5, independent of quenching the reaction mixture with EDTA. From Table 3 it is also evident that the majority (about 70%) of the protein conjugate was eluted from 3-4 mL (fraction 4). This is consistent with Baidoo et. al. reporting 73% yield in the collected PD-10 eluate from 2.5-4.2 mL (1.7 mL). Removal of $^{224}$Ra from the solution containing $^{212}$Pb-TCMC-trastuzumab was quite effective with typically less than 4% $^{224}$Ra remaining in fraction 3-5, with a trend towards more efficient separation when EDTA was used to quench the reaction mixture. It was seen in some of the experiments that $^{224}$Ra started to elute after 4.5 mL, and to minimize the amount of $^{224}$Ra it was decided to exclude fraction 5 from the analysis. The breakthrough of $^{224}$Ra could then be reduced to 0.9±0.8% and 2.7±3.6% with and without EDTA, but came at the expense of a modest reduction in yield of $^{212}$Pb-TCMC-trastuzumab of approximately 5%, to 76.7±11.7% and 76.1±5.9% respectively. ITLC analyses of fraction 4 gave increased RCP of $^{212}$Pb-trastuzumab compared to prior to purification, with an average of 98±1% (n=8). The results altogether indicate that the use of PD-10 purified $^{212}$Pb-trastuzumab prepared from $^{224}$Ra/$^{212}$Pb mixtures is feasible.

To examine whether any of the radionuclides in the $^{224}$Ra-solution bind non-specifically to trastuzumab and thereby co-elute with the protein fractions, an experiment was performed where the radiolabeling protocol and PD-10 purification were performed as usual, except that TCMC-trastuzumab was replaced with trastuzumab. The presence of $^{212}$Bi, $^{212}$Pb and $^{224}$Ra was assessed by measuring the seven collected fractions at different time points after the PD-10 purification was finalized. A percentage of total activities in the 60-110 and 520-640 keV windows, respectively were tested. A significant amount (32%) of $^{212}$Bi co-eluted with the antibody in fractions 4 and 5 when no EDTA was present. It is seen from the decay rate that the activity measured in this window (520-640 keV) clearly originates from ingrowth of $^{208}$Tl from $^{212}$Bi as it decays with the half-life of the mother $^{212}$Bi.

When EDTA was used to quench the reaction mixture, the co-elution of $^{212}$Bi was reduced to 1.3% in the same fractions. Co-elution of $^{212}$Pb was insignificant in fraction 3 and 4 of the PD-10 eluate when EDTA was present, and below 2% in fraction 5. Without EDTA present, approximately 5% of the total $^{212}$Pb activity co-eluted with the antibody in fractions 3-5. As can be seen from the measurements on day 5, co-elution of $^{224}$Ra was negligible (less than 0.7%) in both cases. Altogether, the results clearly show that using EDTA to quench the reaction mixture prior to purification on the PD-10 column maximizes the product purity when a $^{224}$Ra-solution is used for preparing $^{212}$Pb-based radioimmunoconjugates. This measure removes non-specific bound $^{212}$Bi and $^{212}$Pb from the antibody fractions, and at the same time gives less remaining 224Ra in the end product.

It is of interest to have knowledge about the fate of $^{212}$Bi formed when $^{212}$Pb chelated to TCMC decays. In order to avoid radiotoxicity caused by free $^{212}$Bi it is desirable that a substantial fraction of $^{212}$Bi is retained by the TCMC-chelator upon decay. Mirzadeh and colleagues found that 36% of $^{212}$Bi was released from the DOTA-chelator when $^{212}$Pb decayed and they claimed the breakup of the complex was due to internal conversion from γ rays emitted from excited $^{212}$Bi nuclei. We have found no corresponding examination for the retention of $^{212}$Bi by the TCMC-chelator when $^{212}$Pb decays, and therefore made an estimation based on our data. We determined the $^{212}$Bi to $^{212}$Pb ratio in fraction 4 of the PD-10 purified product at different time points after finalizing the purification. Depending on the initial amount of $^{212}$Bi present, the $^{212}$Bi/$^{212}$Pb ratio increases to varying degrees before it reaches a maximum plateau where the nuclides are in transient equilibrium. Under the assumption that all activity in fraction 4 is bound to the antibody-conjugate straight after purification and by taking into account ingrowth of $^{212}$Bi from $^{212}$Pb during the time from finalizing the purification to the time of measurement, it was estimated that a minimum of 60% of the $^{212}$Bi was associated with the TCMC-chelator after $^{212}$Pb decay. The value we found is in good agreement with the previously mentioned data on $^{212}$Bi retention by the DOTA-chelator. It has been claimed that the four N-donor and four O-donor atoms of the TCMC-chelator will provide for good binding abilities with bismuth, and thus the relatively high retention of $^{212}$Bi in the TCMC-chelator is not unlikely.

The current study demonstrates that a TCMC-conjugated monoclonal antibody can be efficiently labeled with $^{212}$Pb from solutions of $^{224}$Ra in equilibrium with progeny. When a concentration of 4 mg per ml of TCMC-trastuzumab was used, the labeling with $^{212}$Pb would be quantitatively after as little as 5 minutes. At this concentration it was also observed that the major part of the $^{212}$Bi would be chelated by the antibody conjugate. Subsequently, the $^{212}$Pb-labeled conjugate can be separated from cationic $^{224}$Ra using desalting gel exclusion separation. In contrast to the current ion exchange based generators, which may be eluted several times (over a period up to 2 weeks), the liquid $^{212}$Pb generator described here is designed for preparation of a single dose only.

With our proposed method, a ready to use $^{224}$Ra solution can be shipped from a centralized supplier to the end user. This is beneficial both from a logistic point of view and because the work required by the end user is reduced and simplified. We believe it is an advantage with our method that the steps involving handling and evaporation of concentrated acid solutions with high radioactivity levels can be completely avoided in the hospital or radiopharmacy setting. An additional benefit with eliminating the acid digestion procedures is that the total preparation time at the hospital will be shorter, since it is only the actual antibody labeling and purification that needs to be performed. Baidoo et al. reported that this part of the process required only 80 min of the total preparation time of an injectable dose of about 210 min. A shorter preparation time reduces the activity loss caused by decay and will therefore lead to a higher amount of $^{212}$Pb administered to the patients. This is beneficial both to limit the amount of free daughter nuclides in the product at time of injection and to minimize the risk of possible problems with radiolysis of the antibody.

On evaluation of our proposed method for radiolabeling of antibodies, it is also important to address the radiation safety requirements. As with all procedures involving open sources of α-emitting radionuclides, precautions must be followed to avoid inhalation or ingestion. All handling should therefore be performed in either a biosafety bench or in a glove-box under negative pressure to protect the worker. This is especially important when handling the $^{224}$Ra-series, because $^{220}$Rn is one of the daughters. The working space also need to be appropriately shielded. One of the $^{224}$Ra-daughters is $^{208}$Tl which has a highly energetic γ-ray of 2.6 MeV with 36% abundance which basically will determine the thickness of the shielding required. Baidoo et al. have described appropriate shielding for activities up to 740 MBq of $^{224}$Ra to be approximately 15 cm of lead. The dose rate at 30 cm distance from a point source of $^{224}$Ra with this activity in equilibrium with daughters will be reduced from approximately 1600 to 3 μSv/h when 15 cm lead shielding is used. Because the $^{212}$Pb-generator solution we have presented here is intended for preparation of a single patient dose, we do not see it as plausible that the shielding requirements will exceed what has been described by Baidoo et al. Even if $^{224}$Ra is present until purification with our method, as opposed to only on the column when working according to the method presented by Baidoo et al., this will not alter the shielding requirements because 99% of the γ-activity in the series originate from $^{212}$Pb and daughters, and especially the previously mentioned high energy γ-ray from $^{208}$Tl. The evaporation steps included in the method described by Baidoo et al. should be performed in a glove-box or in some sort of closed system where the vapor is collected in order to minimize the risk of creating airborne radioactive contaminants and will therefore require dedicated equipment for this process. No such equipment will be required for our proposed method.

As mentioned previously in the discussion, the current study was carried out with relatively low activity levels and radiolytic problems may arise when higher, clinical relevant activity of $^{224}$Ra solution is used. A potential draw-back of using $^{224}$Ra in equilibrium with $^{212}$Pb instead of pure $^{212}$Pb in the radiolabeling reaction, is the elevated radiation dose to the reaction solution due to an increased α-particle activity. The radiation exposure to the antibody-conjugate is likely to be at its highest during the radiolabeling procedure. At that time $^{224}$Ra and all progeny will contribute to the dose, whereas after purification it will mainly be dose delivered from $^{212}$Pb and daughters. The total decay energy (excluding photons) from $^{224}$Ra and progeny is 27.8 MeV, compared to only 8.8 MeV released from decay of $^{212}$Pb and daughters. To expose the antibody to a high radiation dose, after the incubation period of 30 min, we continued to store the $^{212}$Pb-labeled TCMC-trastuzumab in the $^{224}$Ra-solution in equilibrium until a dose of approximately 700 Gy was achieved. Analysis with size-exclusion HPLC showed a peak including 96% of the total radioactivity at a time consistent with intact TCMC-trastuzumab, with less than 1.3 and 2.9% associated with higher and lower molecular weight compounds respectively. The $^{212}$Pb-TCMC-trastuzumab exposed to 700 Gy was also compared with unlabeled TCMC-trastuzumab with detection of absorption at 280 nm. The results showed a peak of molecular weight compounds lower than the IgG when the radiolabeled antibody was analyzed. This peak comprised approximately 11% and was not seen with the unlabeled TCMC-trastuzumab and is therefore likely caused by radiolytic degradation of the protein. The amount of high molecular species was similar between the two samples (less than 1.6%). However, the apparent radiolytic damage to a fraction of the antibody did not seem to influence the immunoreactive fraction of the product. Two samples of $^{212}$Pb-labeled TCMC-trastuzumab exposed to 100 and 700 Gy, was purified with a PD-10 column and the immunoreactivity of fraction 4 was determined to be 60 and 57% respectively, with low (less than 3%) non-specific binding in both cases. This is in accordance with results from the literature, were exposure of up to 1000 Gy was tolerated without significantly reducing the cell binding fraction of an antibody.

Altogether, the examination of possible radiolytic effects at higher radiation doses indicate that the radiation dose to the antibody should be kept below 700 Gy. In the phase I study of intraperitoneally administered $^{212}$Pb-TCMC-trastuzumab the highest dose the patients received was 27.4 MBq/m$^2$. By using an average body surface area of 1.79 m$^2$ found in a study of adult cancer patients this dose corresponds to 49 MBq per patient. To prepare a patient dose with this activity it is reasonable to assume that an activity of 100 MBq $^{224}$Ra should be sufficient as it corresponds to about the double of the highest dose of $^{212}$Pb-TCMC-trastuzumab administered to patients in the phase I trial. The radiation dose to the antibody solution during a 30 min labeling with 100 MBq of $^{224}$Ra in a reaction volume of 1.5 mL, which is compatible with the PD-10 gel exclusion purification format, was estimated to be 534 Gy. Based on these calculations, it is predicted that the method described herein could be useful also in a clinical setting where high activity levels are used.

The purity of $^{212}$Pb vs. $^{224}$Ra is an important quality parameter for the $^{212}$Pb-labeled radioimmunoconjugate. For the in situ labeling method proposed in this paper to be a feasible alternative to the existing protocol, careful consideration must be given to define acceptable limits of $^{224}$Ra in the end product. Fortunately, $^{224}$Ra has been extensively studied both in animals and in humans, and the toxicity profile is well-known. As with other radium-isotopes, after intravenous injection, $^{224}$Ra is mainly deposited in bone. Because of its natural bone seeking properties, it was introduced as a palliative treatment of ankylosing spondylitis already in the 1940s. It was in use for several decades (until 1990), and then briefly re-introduced for the same indication by a different manufacturer from 2000-2005. Dosimetric calculations, performed according to the model proposed by the International Commission on Radiological Protection, showed that the absorbed doses after intravenous injection of $^{224}$Ra-dichloride was highest on the bone surface and red bone marrow since introduction, weekly injections of 1 MBq, up to a total of ten injections, has been used as a treatment regimen in adult patients. Reports including around 1000 patients who received this dose have shown that such amounts of $^{224}$Ra-dichloride can be administered without considerable bone marrow toxicity. These historical data indicate that a 1 MBq of $^{224}$Ra per dosing, or a total of 10 MBq cumulative, might be acceptable in adult patients as long as the $^{212}$Pb product by itself does not produce a high degree of bone marrow toxicity.

In the phase I study of intraperitoneally administered $^{212}$Pb-TCMC-trastuzumab, no significant myelosuppression was found. From the results obtained here, when EDTA was used to quench the reaction mixture before PD-10 purification, the remaining amount of $^{224}$Ra in the end product could be kept below 1%. This corresponds to 0.5 MBq of $^{224}$Ra administered to a patient given 50 MBq of a $^{212}$Pb-based product. A patient dose of approximately 49 MBq was the highest dose of $^{212}$Pb-TCMC-trastuzumab (27.4 MBq/m2) administered in the previously mentioned phase I trial. Altogether, these estimations indicate that a sufficient purity of $^{212}$Pb vs. $^{224}$Ra in the end product of a $^{212}$Pb-labeled radioimmunoconjugate prepared from a $^{224}$Ra solution could be achieved, under the assumption that up to 1 MBq of $^{224}$Ra per dosing is a tolerable amount.

CONCLUSIONS

The current work demonstrates the convenience of a $^{224}$Ra-solution as a shippable generator solution for producing $^{212}$Pb-based radioimmunoconjugates. The generation of $^{212}$Pb-labeled conjugates is easier and less time consuming to use for the end user in comparison with current ion exchange based methods.

The invention claimed is:

1. A method for generating a radionuclide labeled protein, the method comprising:
   a) providing an raw aqueous solution comprising $^{224}$Ra and $^{212}$Pb, and an aqueous solution comprising a protein conjugated with a chelator,
   b) mixing and incubating the solutions provided in a) to provide a reaction solution comprising a $^{212}$Pb-labelled protein,
   c) purifying the reaction solution by gel filtration chromatography to remove $^{224}$Ra, and
   d) recovering the $^{212}$Pb-labelled protein from the purification in step c).

2. The method according to claim 1, wherein the protein is selected from the group consisting of a monoclonal antibody, a polyclonal antibody, an antibody fragment, a synthetic protein, and a peptide.

3. The method according to claim 1, wherein the protein has a size of 500-500,000 Dalton.

4. The method according to claim 1, wherein the solution comprising $^{224}$Ra and $^{212}$Pb in step a) has a radioactivity generated from $^{224}$Ra and $^{212}$Pb of 1 to 10 000 MBq.

5. The method according to claim 1, wherein the activity ratio in MBq between $^{212}$Pb to $^{224}$Ra in the aqueous solution in step a) is between 0.5 and 2.

6. The method according to claim 1, wherein the antibody conjugated with a chelator recovered in step d) is present in amount of 0.05-50 mg.

7. The method according to claim 1, wherein the solution in step a) is in a volume of 100 µL to 1000 mL.

8. The method according to claim 1, wherein the solution comprising an antibody conjugated with a chelator in step a) has a concentration of 0.1 to 4 mg/ml.

9. The method according to claim 1, wherein the mixing and incubating in step b) is done in 1-180 minutes.

10. The method according to claim 1, wherein the gel filtration chromatography in step c) is selected from the group consisting of desalting purification, desalting and buffer exchange, and desalting gel exclusion separation.

11. The method according to claim 1, wherein the desalting is repeated for enhancement of the purity.

12. The method according to claim 1, wherein the purification in step c) is driven by a method selected from the group consisting of centrifugation, pressure, vacuum, and gravitation.

13. The method according to claim 1, wherein the chelator is TCMC.

14. The method according to claim 1, wherein the antibody is selected from the group consisting of trastuzumab, rituximab, HH1, cetuximab, bevacizumab, daratumumab, alemtuzumab, Pembrolizumab, Epratuzumab, L19, F8, F16, Galiximab, Toralizumab, Alemtuzumab, Ofatumumab, Veltuzumab, Afutuzumab, Tositumomab, Reditux and Ibritumomab.

15. The method according to claim 1, wherein the protein is an antibody that is specific for an antigen selected from the group consisting of CD19, CD20, CD22, CD33, CD37, CD38, CD45, CD74, CD138, PSMA, HER-2, EGFR, MUC-1, MUC-18, CEA, FBP, NG2, EPCAM, Syndecan-1, Ca-125, LK-26, HMFG, CS-1, and BCMA.

* * * * *